(12) United States Patent
Lin (10) Patent No.: US 9,492,254 B2
(45) Date of Patent: Nov. 15, 2016

(54) FOLDABLE AND FLEXIBLE ULTRASONIC VIBRATION MASK FOR TEETH CLEANING

(71) Applicant: CHUNG HUA UNIVERSITY, Hsinchu (TW)

(72) Inventor: Jium Ming Lin, Hsinchu (TW)

(73) Assignee: CHUNG HUA UNIVERSITY, Hsinchu (TW)

( * ) Notice: Subject to any disclaimer, the term of this patent is extended or adjusted under 35 U.S.C. 154(b) by 239 days.

(21) Appl. No.: 14/447,998

(22) Filed: Jul. 31, 2014

(65) Prior Publication Data

US 2016/0030143 A1 Feb. 4, 2016

(51) Int. Cl.
*A61C 1/00* (2006.01)
*A61C 17/20* (2006.01)

(52) U.S. Cl.
CPC .................. *A61C 17/20* (2013.01)

(58) Field of Classification Search
CPC .............. A61C 17/20; A41D 13/1107
See application file for complete search history.

(56) References Cited

U.S. PATENT DOCUMENTS

2005/0244792 A1 11/2005 Verdi et al.
2015/0072306 A1* 3/2015 Barnard .............. A61C 17/20
433/98

FOREIGN PATENT DOCUMENTS

TW 200904384 A 2/2009

OTHER PUBLICATIONS

Office Action and search report dated Sep. 11, 2015 from the Taiwan counterpart application 103126142.
English abstract translation of the office Action dated Sep. 11, 2015 from the Taiwan counterpart application 103126142.
English abstract translation of TW200904384A.

\* cited by examiner

*Primary Examiner* — Robert N Wieland
(74) *Attorney, Agent, or Firm* — WPAT, P.C., Intellectual Property Attorneys; Anthony King (57) ABSTRACT

A foldable and flexible ultrasonic vibration mask for cleaning teeth comprises two upper devices and two lower devices. Each upper device comprises a flexible substrate, coils configured to generate ultrasonic sound and formed on the flexible substrate, coils configured to generate audible sound and formed on the flexible substrate, a resonance chamber attached to the flexible substrate and including a magnetic alloy. Each lower device includes a flexible substrate, coils configured to generate ultrasonic sound and formed on the flexible substrate, and a resonance chamber attached to the flexible substrate and including a magnetic alloy. The flexible substrates of the two upper devices are fixed together. The flexible substrates of each upper device and a corresponding lower device are fixed together. The flexible substrates of the two lower devices are fixed together.

10 Claims, 10 Drawing Sheets

FOLDABLE AND FLEXIBLE ULTRASONIC VIBRATION MASK FOR TEETH CLEANING

BACKGROUND

1. Technical Field

The present invention relates to a foldable and flexible ultrasonic vibration mask for cleaning teeth.

2. Related Art

Periodontal disease may cause teeth to become loose, resulting in incomplete chewing of food and affecting digestion of food. In addition, periodontal disease may adversely affect cardiovascular health. Thus, periodontal disease has a strong connection with people's health. In order to clean teeth completely, many electric toothbrushes incorporate ultrasonic technology to achieve better cleaning results.

However, traditional electric toothbrushes need a hand to insert brushes into mouths, and then use ultrasonic waves to clean teeth. During brushing, teeth are cleaned one after another. The process is tedious and needs extended time in order to complete the process. The electric toothbrushes need a hand to operate, and thus, the hand is not available to do other things. Therefore, it causes an inconvenience to busy modern people.

SUMMARY

In one embodiment, a foldable and flexible ultrasonic vibration mask for cleaning teeth comprises a first device, a second device, a third device, and a fourth device. The first device comprises a flexible substrate, a plurality of first coils formed on the flexible substrate and configured to generate ultrasonic waves, at least one second coil formed on the flexible substrate and configured to generate audible sound, and a resonance chamber including magnetic alloy materials disposed correspondingly to the first coils and the second coil, wherein the flexible substrate is attached to the resonance chamber. The second device comprises a flexible substrate, a plurality of coils configured to generate ultrasonic waves and formed on the flexible substrate of the second device, and a resonance chamber including magnetic alloy materials disposed correspondingly to the coils of the second device, wherein the flexible substrate of the second device is attached to the resonance chamber of the second device, and the flexible substrate of the first device is attached to the flexible substrate of the second device. The third device comprises a flexible substrate, a plurality of first coils configured to generate ultrasonic waves and formed on the flexible substrate of the third device, at least one second coil configured to generate audible sound and formed on the flexible substrate of the third device, and a resonance chamber including magnetic alloy materials disposed correspondingly to the first coils and the second coil of the third device, wherein the flexible substrate of the third device is attached to the resonance chamber of the third device, and the flexible substrate of the third device is attached to the flexible substrate of the first device. The fourth device comprises a flexible substrate, a plurality of coils configured to generate ultrasonic waves and formed on the flexible substrate of the fourth device, and a resonance chamber including magnetic alloy materials disposed correspondingly to the coils of the fourth device, wherein the flexible substrate of the fourth device is attached to the resonance of the fourth device, wherein the flexible substrate of the fourth device is attached to the flexible substrate of the second device, and the flexible substrate of the fourth device is attached to the flexible substrate of the third device.

To better understand the above-described objectives, characteristics and advantages of the present invention, embodiments, with reference to the drawings, are provided for detailed explanations.

BRIEF DESCRIPTION OF THE DRAWINGS

The invention will be described according to the appended drawings in which.

DETAILED DESCRIPTION OF DISCLOSED EMBODIMENTS

The following description is presented to enable any person skilled in the art to make and use the disclosed embodiments, and is provided in the context of a particular application and its requirements. Various modifications to the disclosed embodiments will be readily apparent to those skilled in the art, and the general principles defined herein may be applied to other embodiments and applications without departing from the spirit and scope of the disclosed embodiments. Thus, the disclosed embodiments are not limited to the embodiments shown, but are to be accorded the widest scope consistent with the principles and features disclosed herein.

Figure 1:
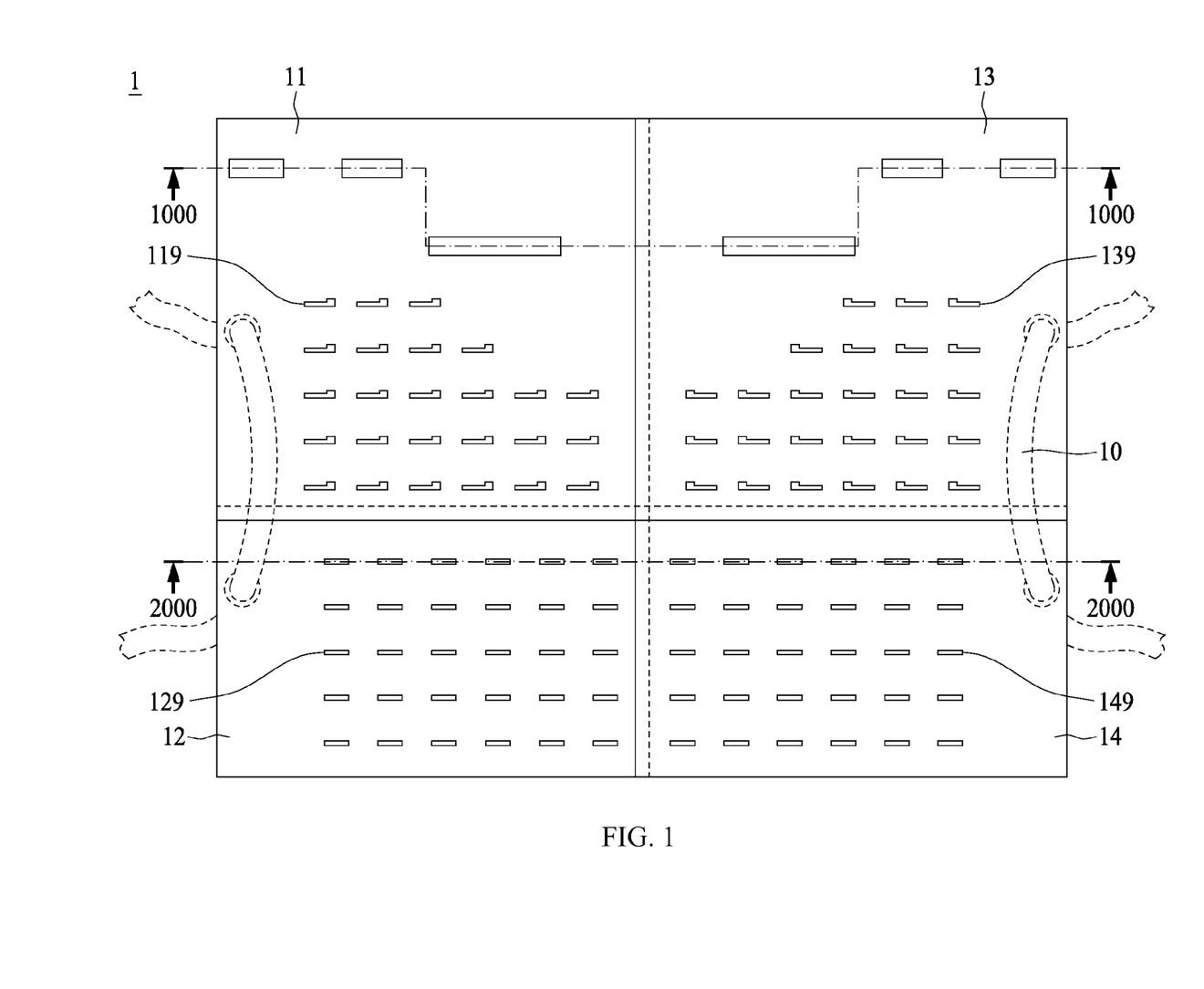
FIG. 1 is a view showing a foldable and flexible ultrasonic vibration mask for cleaning teeth according to one embodiment of the present invention.
Figure 2:
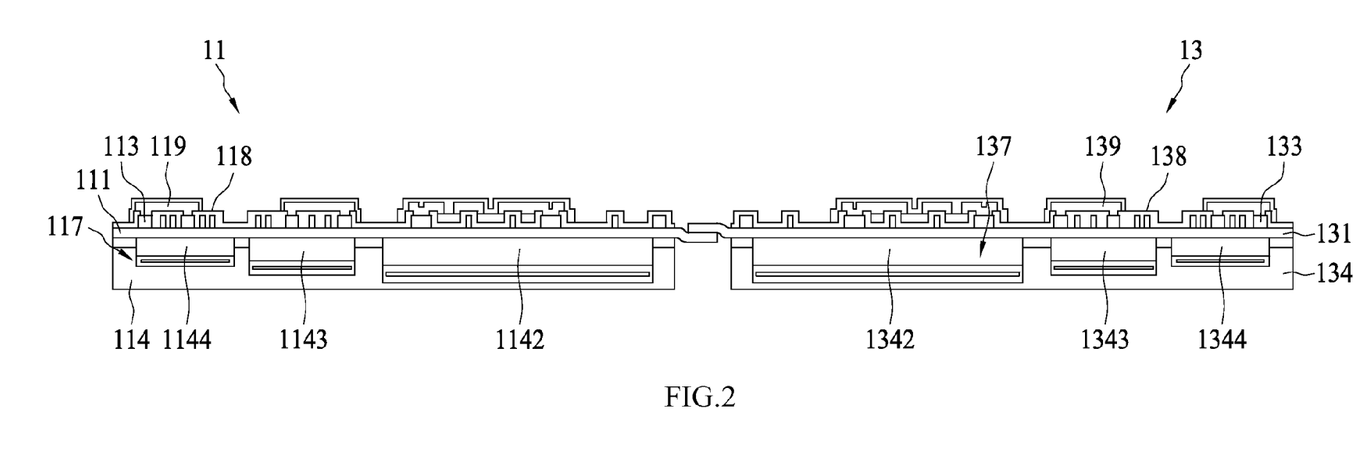
FIG. 2 is a cross-sectional view along line 1000-1000 of FIG. 1.
Figure 3:
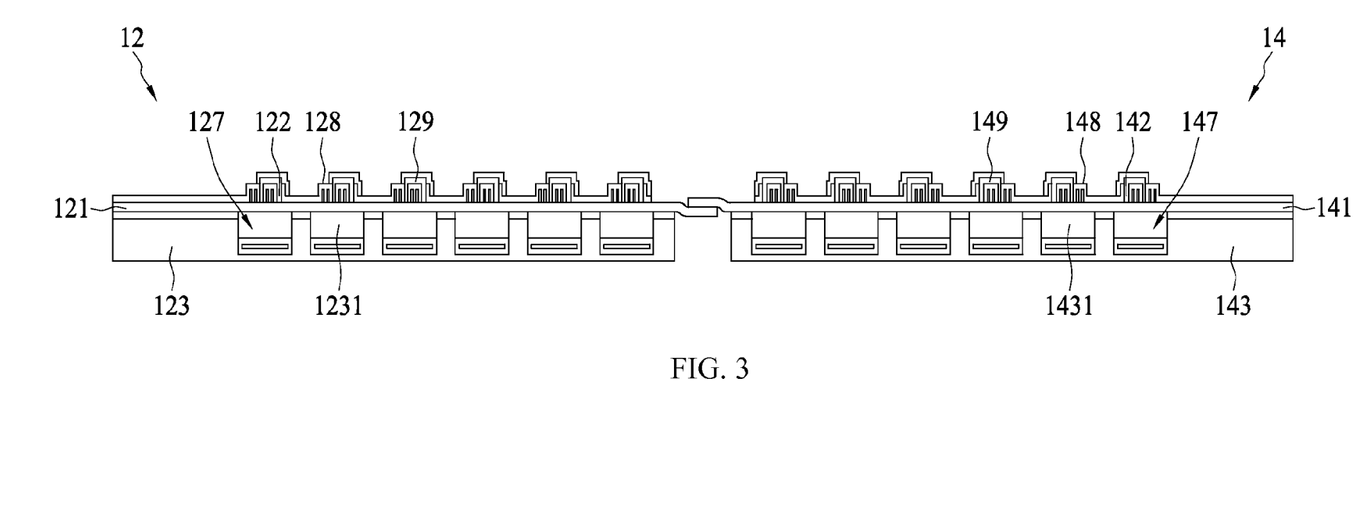
FIG. 3 is a cross-sectional view along line 2000-2000 of FIG. 3.

FIG. 1 is a view showing a foldable and flexible ultrasonic vibration mask for cleaning teeth according to one embodiment of the present invention. FIG. 2 is a cross-sectional view along line 1000-1000 of FIG. 1. FIG. 3 is a cross-sectional view along line 2000-2000 of FIG. 1.

In at least one embodiment, a foldable and flexible ultrasonic vibration mask for cleaning teeth comprises a first device 11, a second device 12, a third device 13, and a fourth device 14. The mask 1 is wearable or held on a face. The mask 1 can cover cheeks. The mask 1 can cover lower jaws. The first device 11 can generate ultrasonic waves to clean teeth. The first device 11 can generate audible sounds. The second device 12 can generate ultrasonic waves. The third device 13 can generate ultrasonic waves. The third device 13 can generate audible sounds. The fourth device 14 can generate ultrasonic waves. The third device 13 and the first device 11 can cover cheeks. The second device 12 and the fourth device 14 can cover a lower jaw. The first device 11, the second device 12, the third device 13, and the fourth device 14 can be separately formed and then assembled together; however, the present invention is not limited to such a process.

Figure 4:
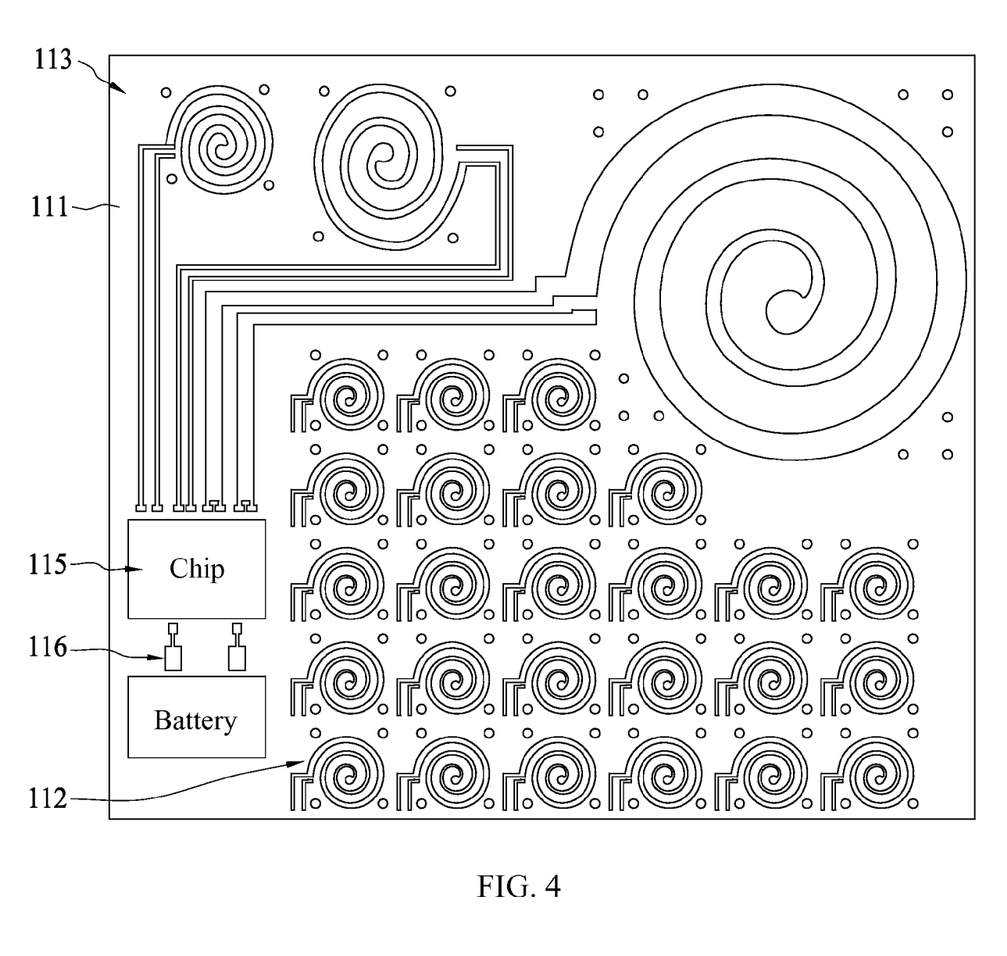
FIG. 4 is a view showing a portion of electronic components of the first device according to one embodiment of the present invention.
Figure 5:
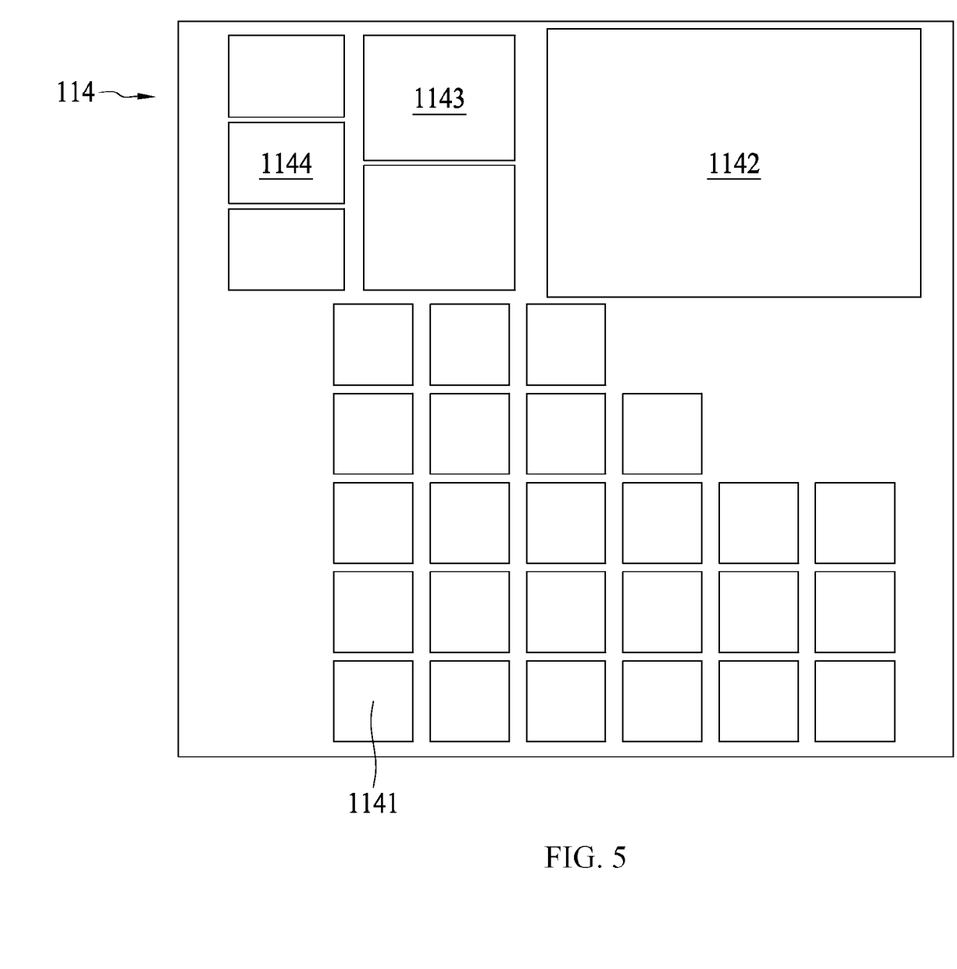
FIG. 5 is a view showing a resonance chamber of a first device according to one embodiment of the present invention.

FIG. 4 is a view showing a portion of electronic components of a first device 11 according to one embodiment of the present invention. FIG. 5 is a view showing a resonance chamber of a first device 11 according to one embodiment of the present invention.

Referring to FIGS. 2, 4, and 5, the first device 11 comprises a flexible substrate 111, a plurality of first coils 112, at least one second coil 113, and a resonance chamber 114. The plurality of first coils 112 and the least one second coil 113 are formed on the flexible substrate 111. The plurality of first coils 112 include micro-coils. The first coil 112 is configured to generate ultrasonic waves. The second coil 113 is configured to generate audible sounds. The flexible substrate 111 is attached to the resonance chamber 114. The flexible substrate 111 can be laminated onto the resonance chamber 114. The flexible substrate 111 can be glued onto the resonance chamber 114. In some embodiments, the at least one second coil 113 comprises large, middle, and small coils, which are respectively configured to generate audible sounds with low, middle, and high frequencies.

The resonance chamber 114 can be partitioned into a plurality of micro-cavities 1141 disposed correspondingly to the plurality of first coils 112. In some embodiments, the at least one second coil 113 comprises a large coil and the resonance chamber 114 comprises a correspondingly disposed large cavity 1142. In some embodiments, the at least one second coil 113 comprises two middle coils and the resonance chamber 114 includes two correspondingly disposed and separated middle cavities 1143, wherein the two middle coils are respectively located over the two cavities 1143. In some embodiments, the at least one second coil 113 comprises a small coil and the resonance chamber 114 comprises a plurality of cavities 1144, wherein the small coil is disposed over the plurality of cavities 1144.

Referring to FIG. 2, the resonance chamber 114 comprises magnetic alloy materials 117 disposed correspondingly to the first coils 112 and the second coil 113. The first coil 112 can generate a magnetic field and a reverse magnetic field. The magnetic field and the reverse magnetic field interact with the magnetic field of the below magnetic alloy material, causing attraction and repulsion of the magnetic alloy material and an unfixed portion of the flexible substrate 111 above the corresponding cavity 1141, resulting in generating ultrasonic waves. In some embodiments, a peripheral portion of a flexible substrate 111 around an unfixed portion of the flexible substrate 111 above a corresponding cavity 1141 can be fixed. The second coil 113 can generate a magnetic field and a reverse magnetic field, which can interact with the magnetic field of the below magnetic alloy material and causes attraction and repulsion of the magnetic alloy material and an unfixed portion of the flexible substrate 111 above the corresponding cavity (1142, 1143 or 1144). As a result, audible sounds are generated. In some embodiments, the resonance chamber 114 includes a magnetic alloy plate. In some embodiments, on the bottom of each cavity (1142, 1143, or 1144) is disposed a magnetic alloy plate. In some embodiments, the magnetic alloy plate has a thickness of from 100 to 1000 micrometers; however, the present invention is not limited to such a range. In some embodiments, the magnetic alloy plate comprises iron, cobalt and nickel; however, the present invention is not limited to the aforementioned materials.

In some embodiments, the first coil 112 and the second coil 113 comprise silver. In some embodiments, the first coil 112 and the second coil 113 comprise a polymer and silver. In some embodiments, the first coil 112 and the second coil 113 are made of a silver paste. In some embodiments, the first coil 112 and the second coil 113 comprise gold, chromium, nickel, or a combination thereof. In some embodiments, the first coil 112 or the second coil 113 has a thickness of from 10 to 100 micrometers; however, the present invention is not limited to such a range.

Referring to FIG. 4, the first device 11 comprises a chip 115. The chip 115 is disposed on the flexible substrate 11 and coupled with the first coils 112 and the second coil 113. The chip 115 is configured to supply currents for the first coils 112 (not drawn) and the second coil 113. In some embodiments, the chip 115 comprises a wireless communications component, such as a RFID component, a ZIGBEE component, or a Bluetooth component, whereby the chip 115 can be wirelessly controlled. The chip may include a universal signal-and-function generator. The chip is configured to be remotely controlled so as to set up a waveform (such as a sine waveform, a square waveform, a saw tooth waveform, or a pulse waveform) for generating ultrasonic waves, a vibration frequency, a vibration time, and a duty cycle of a waveform, as shown in Table 1.

TABLE 1

Bit definition for waveforms (including a sine waveform, a square waveform, a saw tooth waveform, or a pulse waveform), vibration frequency, vibration time, and duty cycle.

| | bit | | | | | | | |
|---|---|---|---|---|---|---|---|---|
| | 7 | 6 | 5 | 4 | 3 | 2 | 1 | 0 |
| item | duty cycle | duty cycle | frequency | frequency | time | time | waveform | waveform |

(1) Bit 0-1 (waveform setup): 00: sine waveform; 01: square waveform; 10: saw tooth waveform; 11: pulse waveform.
(2) Bit 2-3 (time setup): 00: one minute; 01: two minutes; 10: three minutes; 11: four minutes.
(3) Bit 4-5 (frequency setup): 00: 30 KHz; 01: 40 KHz; 10: 50 KHz; 11: 60 KHz.
(4) Bit 6-7 (duty cycle setup): 00: 10%; 01: 25%; 10: 50%; 11: 75%.

In some embodiments, the chip 115 comprises a non-volatile memory, such as an electrical erasable and programmable read-only memory or a flash memory. In some embodiments, the non-volatile memory of the chip 115 can store a music file, and the chip 115 can convert the music file into an audio signal and provide currents for the at least one second coil 113 so as to produce sound according to the audio signal. In some embodiments, the chip 115 comprises an amplifier configured to amplify a signal for generating audible sound or ultrasonic waves.

Referring to FIG. 4, the first device 11 includes battery pads 116 coupled with the chip 115. A battery can connect with the pads 116 to provide electricity for the chip 115.

Figure 6:
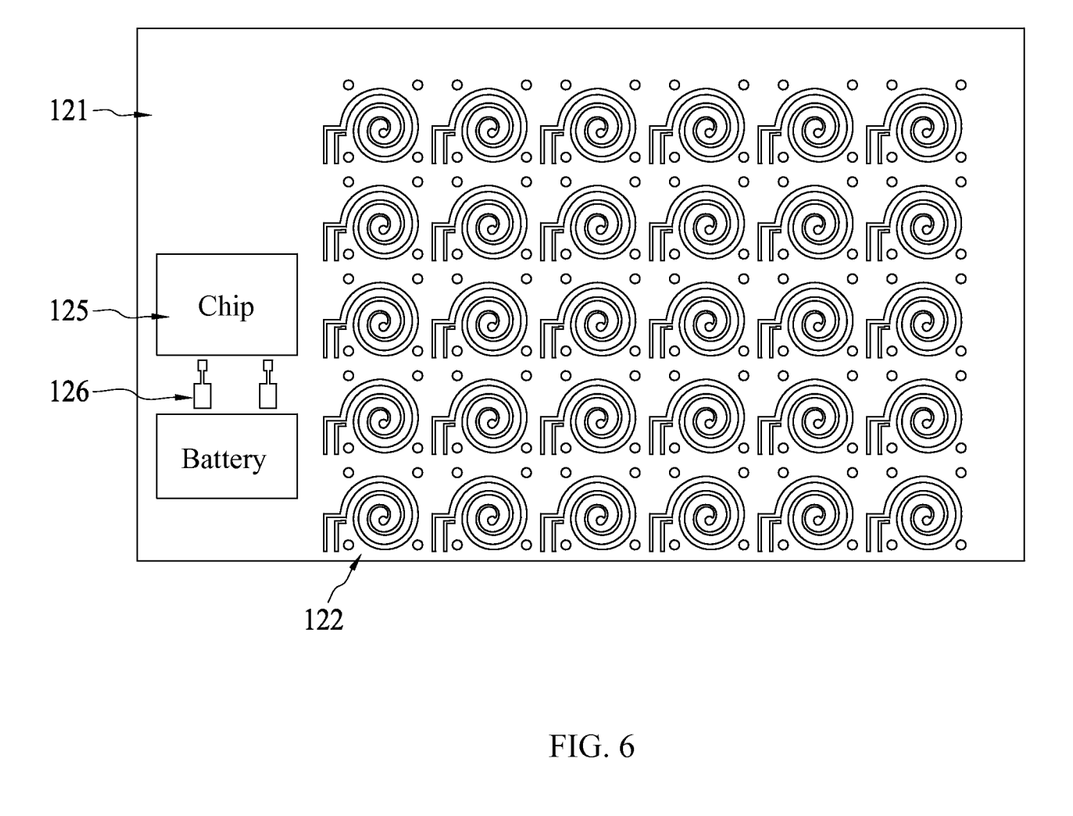
FIG. 6 is a view showing a portion of electronic components of a second device according to one embodiment of the present invention.
Figure 7:
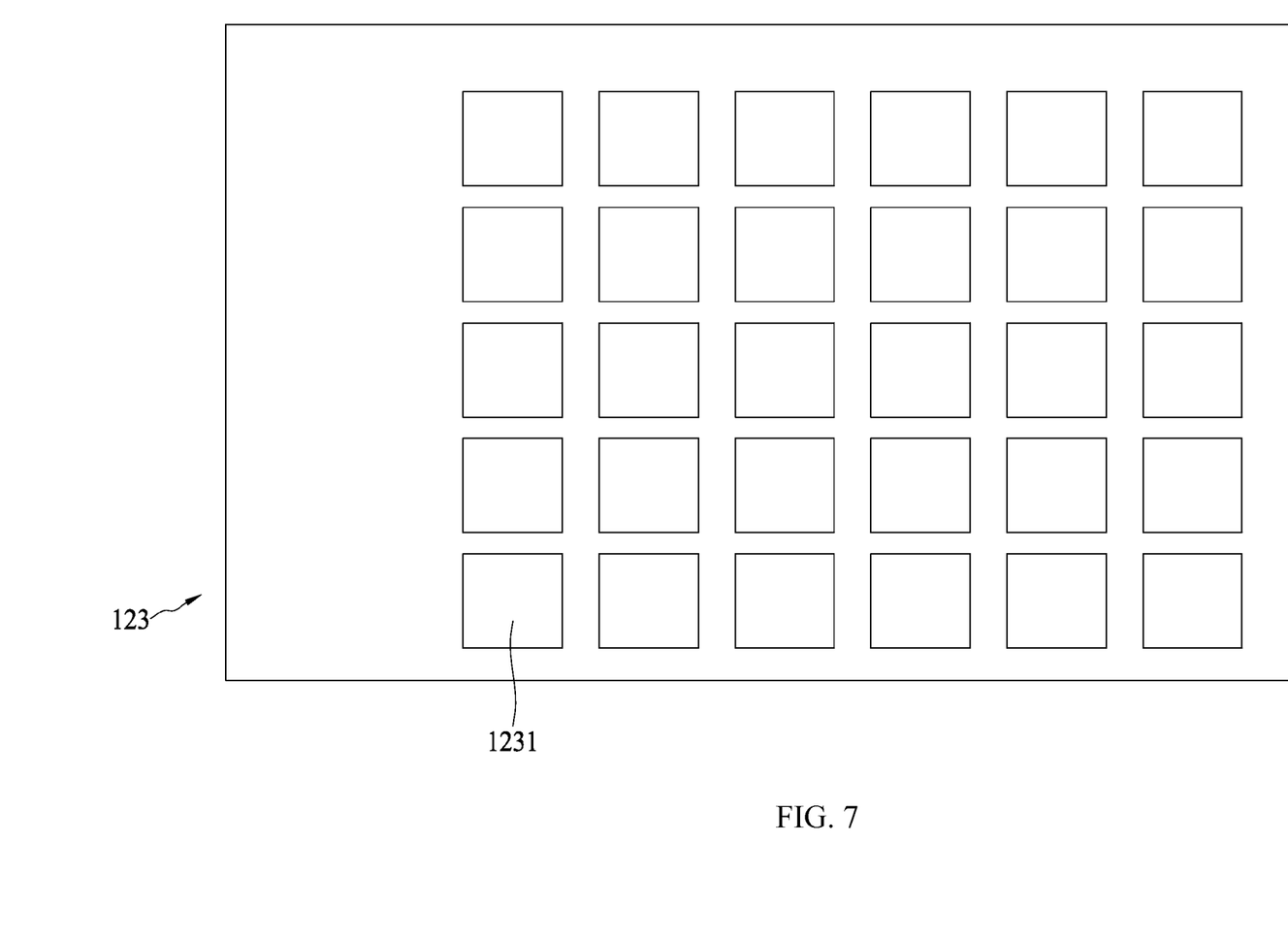
FIG. 7 is a view showing a resonance chamber of a second device according to one embodiment of the present invention.

FIG. 6 is a view showing a portion of electronic components of a second device 12 according to one embodiment of the present invention. FIG. 7 is a view showing a resonance chamber of a second device 12 according to one embodiment of the present invention.

Referring to FIGS. 3, 6, and 7, the second device 12 comprises a flexible substrate 121, a plurality of coils 122, and a resonance chamber 123. The coils 122 can be micro-coils. The coils 122 can be used to generate ultrasonic waves. The coils 122 are formed on the flexible substrate 121. The flexible substrate 121 can be attached to the resonance chamber 123. The flexible substrate 121 can be laminated to the resonance chamber 123. The flexible substrate 121 can be glued onto the resonance chamber 123. In some embodiments, the coil 122 comprises silver. In some embodiments, the coil 122 comprises a polymer and silver. In some embodiments, the coil 122 is made of a silver paste. In some embodiments, the coil 122 comprises gold, chromium, nickel, or a combination thereof; however, the present invention is not limited to the afore-mentioned materials. In some embodiments, the coil 122 has a thickness of 10 to 100 micrometers; however, the present invention is not limited to such a range.

Referring to FIG. 1, the flexible substrate 121 of the second device 12 is attached to or bonded with the flexible substrate 111 of the first device 11. In some embodiments, the flexible substrate 121 of the second device 12 is attached to the flexible substrate 111 of the first device 11 by thermal bonding.

The resonance chamber 123 is partitioned into a plurality of micro-cavities 1231 disposed correspondingly to the plurality of coils 122. The resonance chamber 123 comprises magnetic alloy materials 127 disposed correspondingly to the plurality of coils 122, as shown in FIG. 3. In some embodiments, a magnetic alloy plate is disposed on the bottom of each cavity 123. In some embodiments, the magnetic alloy plate has a thickness of from 100 to 1000 micrometers; however, the present invention is not limited to the afore-mentioned numerical range. In some embodiments, the magnetic alloy plate comprises iron, cobalt, or nickel; however, the present invention is not limited to the afore-mentioned materials.

Referring to FIG. 6, the second device 12 comprises a chip 125. The chip 125 may be disposed on the flexible substrate 121. The chip 125 may be coupled with a plurality of coils 122 (not drawn) so as to provide currents for the coils. In some embodiments, the chip 125 comprises a wireless communications component, such as a RFID component, a ZIGBEE component, or a Bluetooth component, whereby the chip 125 can be wirelessly controlled. The second device 12 may comprise battery pads 126. The pads 126 may be coupled with the chip 125. A battery may connect with the pads 126, and thereby provide electricity for the chip 125.

Figure 8:
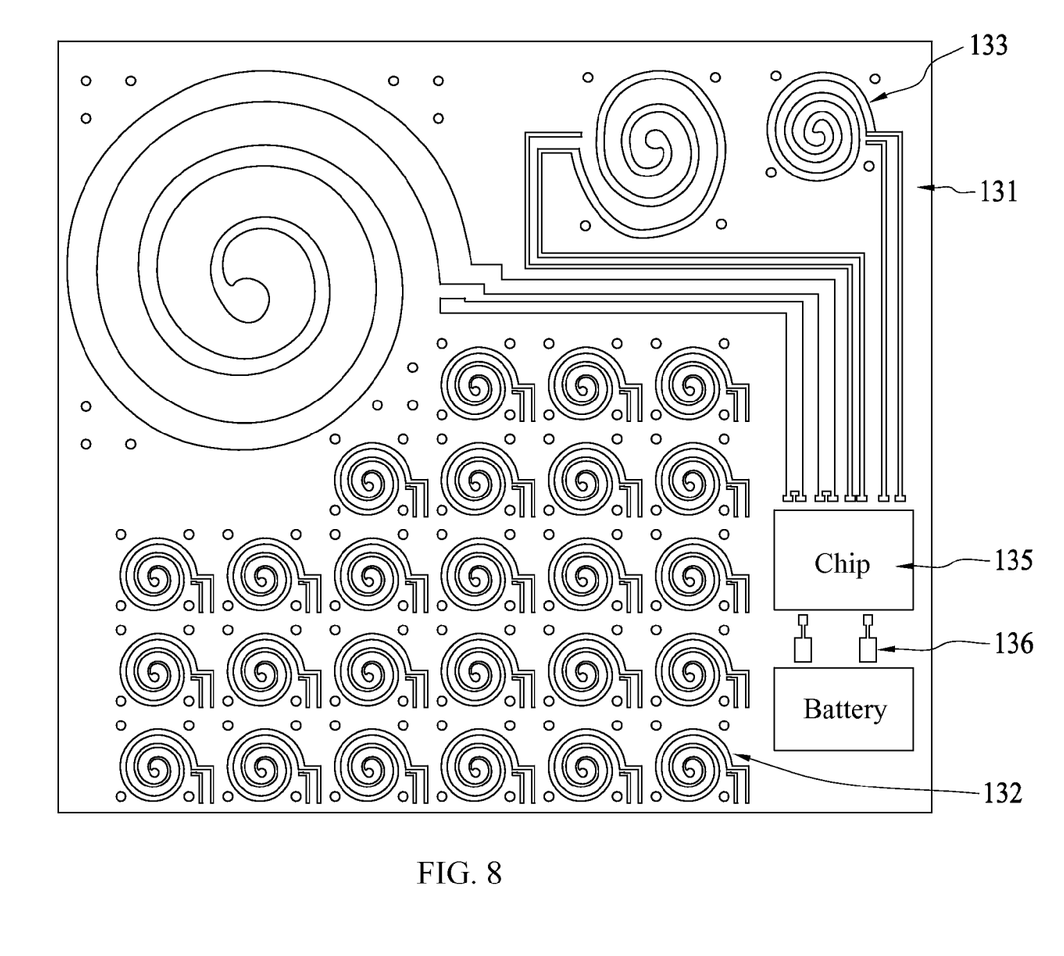
FIG. 8 is a view showing a portion of electronic components of a third device according to one embodiment of the present invention.
Figure 9:
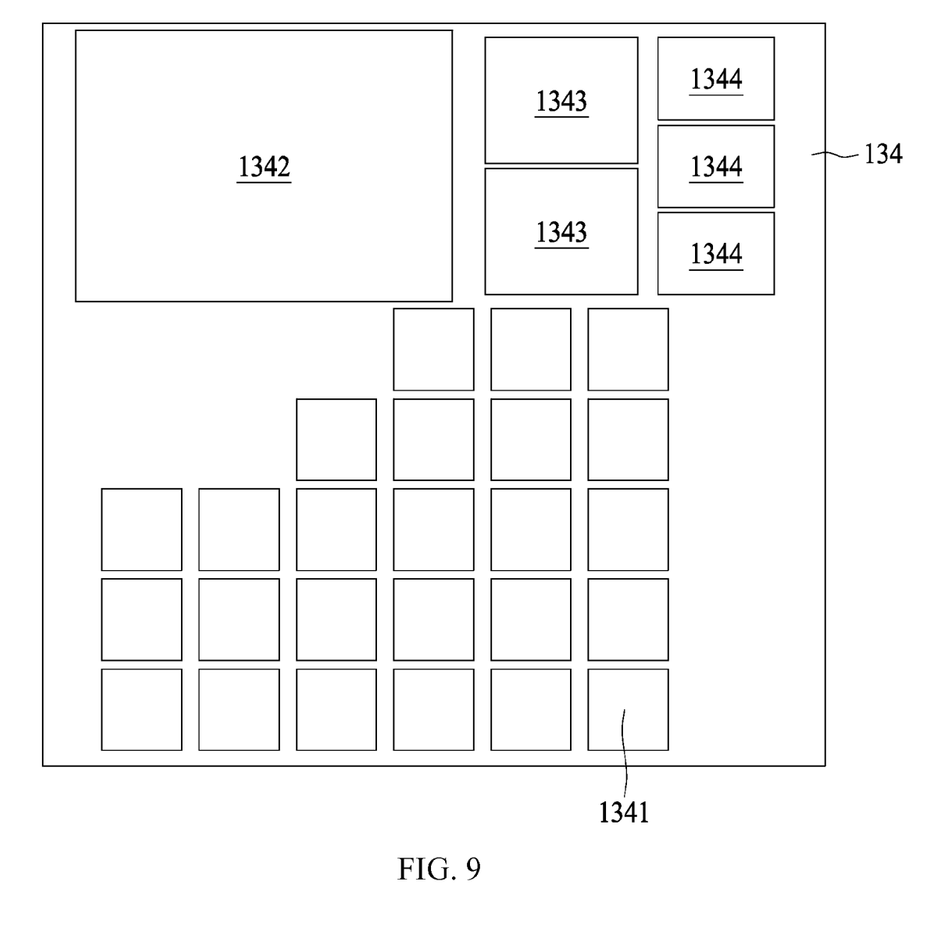
FIG. 9 is a view showing a resonance chamber of a third device according to one embodiment of the present invention.

FIG. 8 is a view showing a portion of electronic components of a third device 13 according to one embodiment of the present invention. FIG. 9 is a view showing a resonance chamber of a third device 13 according to one embodiment of the present invention.

Referring to FIGS. 2, 8, and 9, the third device 13 is similar to the first device 11. The third device 13 comprises a flexible substrate 131, a plurality of first coils 132, at least one second coil 133, and a resonance chamber 134. The plurality of first coils 132 and the at least one second coil 133 are formed on the flexible substrate 131. The first coil 132 is a micro-coil. The first coil 132 is configured to generate ultrasonic waves. The second coil 133 is configured to generate audible sound. The flexible substrate 131 is attached to the resonance chamber 134. The flexible substrate 131 is laminated onto the resonance chamber 134. The flexible substrate 131 can be glued to the resonance chamber 134. In some embodiments, the at least one second coil 133 comprises large, middle, and small coils, which are configured to generate sounds with low, middle, and high frequencies.

The resonance chamber 134 is partitioned into a plurality of micro-cavities 1341 and at least one cavity (1342, 1343, or 1344). The plurality of micro-cavities 1341 are disposed correspondingly to the plurality of first coils 132. The at least one cavity (1342, 1343, or 1344) is disposed correspondingly to the at least one second coil 133. In some embodiments, the at least one second coil 133 comprises large, middle, and small coils, wherein a large coil is disposed correspondingly to one large cavity 1342 of the resonance chamber 134, each middle coil 133 correspond to a middle cavity 1343 in the resonance chamber 134, and a small coil is disposed correspondingly to one small cavity 1344.

Referring to FIGS. 2, 8, and 9, the resonance chamber 134 comprises magnetic alloy materials 137 disposed correspondingly to the first coils 132 and at least one second coil 133. In some embodiments, the resonance chamber 134 is formed as a magnetic alloy plate. In some embodiments, a magnetic alloy material 137 is disposed on the bottom of each cavity (1341, 1342, 1343, or 1344). In some embodiments, the magnetic alloy plate has a thickness of 100 to 1000 micrometers; however, the present invention is not limited to such a thickness range. In some embodiments, the magnetic alloy plate comprises iron, cobalt, or nickel; however, the present invention is not limited to the afore-mentioned materials.

In some embodiments, the first coil 132 and the second coil 133 comprise silver. In some embodiments, the first coil 132 and the second coil 133 comprise a polymer and silver. In some embodiments, the first coil 132 and the second coil 133 are made of a silver paste. In some embodiments, the first coil 132 and the second coil 133 comprise gold, chromium, nickel, or a combination thereof. In some embodiments, the first coil 132 and the second coil 133 have a thickness of 10 to 100 micrometers; however, the present invention is not limited to such a range.

Referring to FIG. 8, the third device 13 comprises a chip 135, which is disposed on the flexible substrate 131 and coupled with the first coils 132 (not drawn) and the second coil 133. The chip 135 is configured to provide electricity for the plurality of first coils 132 and at least one second coil 133. In some embodiments, the chip 135 comprises a wireless communications component, such as a RFID component, a ZIGBEE component, or a Bluetooth component, whereby the chip 135 can conduct wireless communications. In some embodiments, the chip 135 comprises a non-volatile memory, such as an electrical erasable and programmable read-only memory or a flash memory. In some embodiments, the memory of the chip 135 can store a music file, and the chip 135 can convert the music file into an audio signal and provide currents for the at least one second coil 133 so as to produce sound according to the audio signal. In some embodiments, the chip 135 comprises an amplifier configured to amplify a signal for generating audible sound or ultrasonic waves.

Referring to FIG. 8, the third device 13 includes battery pads 136 configured to connect with a battery so as to supply electricity to the chip 135.

Referring to FIG. 1, the third device 13 comprises a flexible substrate 131 bonded with the flexible substrate 111 of the first device 11. In some embodiments, the flexible substrate 131 of the third device 13 is attached to the flexible substrate 111 of the first device 11 by thermal bonding.

Figure 10:
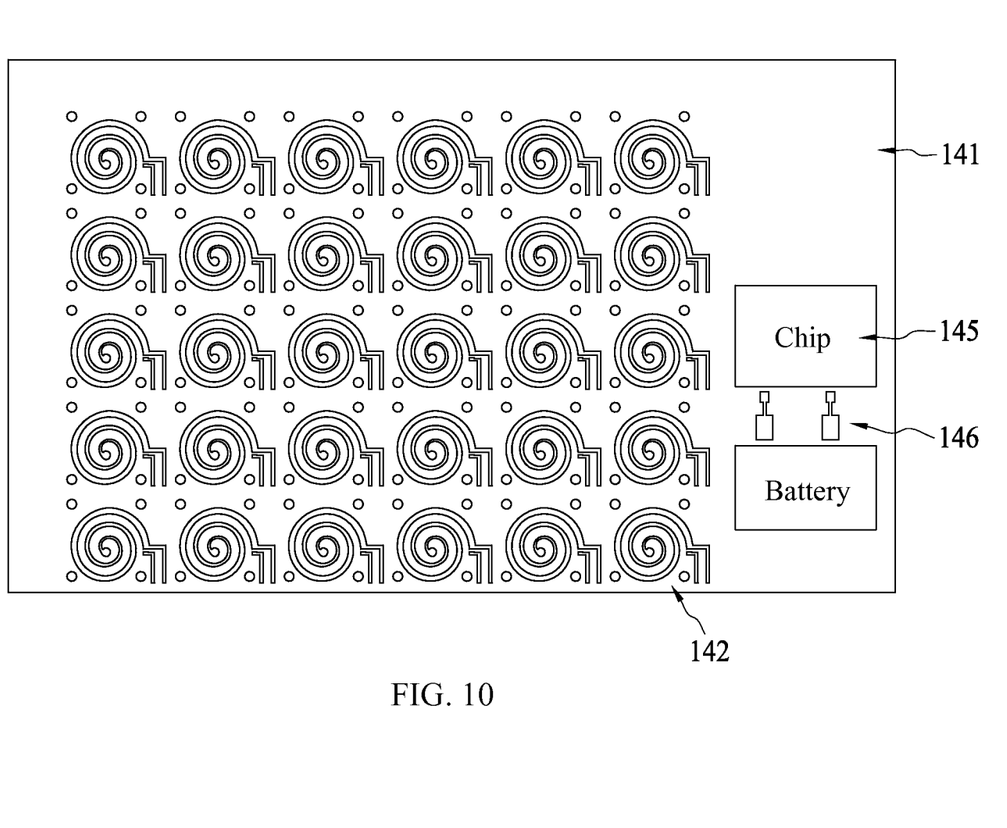
FIG. 10 is a view showing a portion of electronic components of a fourth device according to one embodiment of the present invention.
Figure 11:
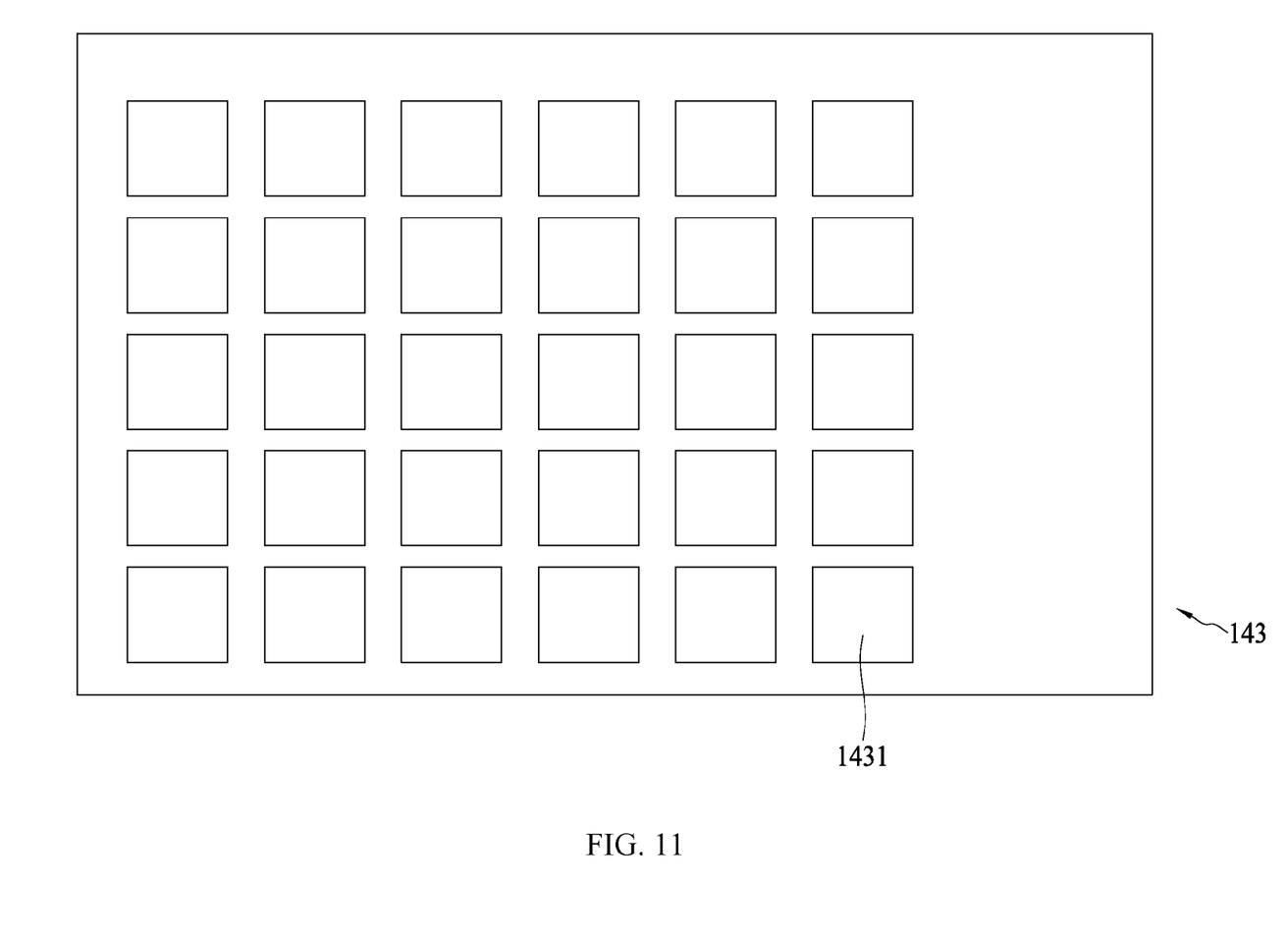
FIG. 11 is a view showing a resonance chamber of a fourth device according to one embodiment of the present invention.

FIG. 10 is a view showing a fourth device according to one embodiment of the present invention. FIG. 11 is a view showing another portion of the a device according to one embodiment of the present invention.

Referring to FIGS. 3, 9 and 10, the fourth device 14 is similar to the second device 12. The fourth device 14 comprises a flexible substrate 141, a plurality of coils 142, and a resonance chamber 143. The coils 142 can be microcoils. The coils 142 are configured to generate ultrasonic waves. The coils 142 are formed on the flexible substrate 141. The flexible substrate 141 can be laminated onto the resonance chamber 143. The flexible substrate 141 is glued to the resonance chamber 143. In some embodiments, the coil 142 comprises silver. In some embodiments, the coil 142 comprises a polymer and silver. In some embodiments, the coil 142 is made of a silver paste. In some embodiments, the coil 142 comprises gold, chromium, nickel, or a combination thereof. In some embodiments, the coil 142 has a thickness of from 10 to 1000 micrometers; however, the present invention is not limited to such a range.

Referring to FIG. 1, the flexible substrate 141 of the fourth device 14 is attached to the flexible substrate 131 of the third device 13. In some embodiments, the flexible substrate 141 of the fourth device 14 is attached to the flexible substrate 131 of the third device 13 by thermal bonding.

The flexible substrate 141 of the fourth device 14 is attached to the flexible substrate 121 of the second device 12. In some embodiments, the flexible substrate 141 of the fourth device 14 is attached to the flexible substrate 121 of the second device 12 by thermal bonding.

Referring to FIGS. 3 and 11, the resonance chamber 143 comprises a plurality of micro-cavities 1431 disposed correspondingly to the plurality of coils 142. The resonance chamber 143 comprises magnetic alloy materials 147 disposed correspondingly to the plurality of coils 142. In some embodiments, a magnetic alloy material is disposed on the bottom of each cavity 1431. In some embodiments, the magnetic alloy material has a thickness of from 100 to 1000 micrometers; however, the present invention is not limited to such a range. In some embodiments, the magnetic alloy material comprises iron, cobalt, nickel, or a combination thereof; however, the present invention is not limited to the afore-mentioned materials.

Referring to FIG. 10, the fourth device 14 comprises a chip 145. The chip 145 is disposed on the substrate 141 and coupled with a plurality of coils 142 so as to provide electricity for the plurality of coils 142. In some embodiments, the chip 145 comprises a wireless communications component, such as a RFID component, a ZIGBEE component, or a Bluetooth component, whereby the chip 145 can be remotely controlled. The fourth device 14 comprises battery pads 146 coupled with the chip 145. The pads 146 can connect with a battery, which can supply electricity to the chip 145.

In some embodiments, when the mask 1 is worn, the first device 11 and the third device 13 covers cheeks; and the second device 12 and the fourth device 14 covers a lower jaw. In some embodiments, the cavities (1141, 1142, 1143, and 1144) of the resonance chamber 114 of the first device 11 and the cavities (1341, 1342, 1343, and 1344) of the third device 13 are disposed symmetrically.

In some embodiments, the flexible substrate (111, 121, 131, or 141) can include a plurality of openings. During vibration of the flexible substrate (111, 121, 131, or 141), air can flow through plurality of openings so that a vibration effect can be enhanced. In some embodiments, at least one opening can be formed adjacent to each coil of each flexible substrate.

In some embodiments, the chip 115, 125, 135, or 145 is configured to be able to set up a time for cleaning teeth.

Referring to FIGS. 2 and 3, each of the first device 11, the second device 12, the third device 13, and the fourth device 14 comprises an insulating layer (118, 128, 138, or 148). The insulating layer (118, 128, 138, or 148) correspondingly fills vacancy in or between the coils of the first device 11, the second device 12, the third device 13, or the fourth device 14, and at least partially covers corresponding coils. In some embodiments, the insulating layer (118, 128, 138, or 148) comprises a negative photoresist or polyimide layer with a thickness of from 0.5 to 10 micrometers; however, the present invention is not limited to such embodiments. In addition, an inner end portion of each coil of the first device 11, the second device 12, the third device 13, or the fourth device 14 connects to a conductor (119, 129, 139, or 149). The conductor (119, 129, 139, or 149) may be formed over the corresponding insulating layer (118, 128, 138, or 148) and extends toward the outside of a corresponding coil so that the inner end portion can connect to a corresponding chip (115, 125, 135, or 145). In some embodiments, the conductor (119, 129, 139, or 149) can be formed by screen-printing.

In some embodiments, the first device 11 and the third device 13 respectively comprise a D-type connector. In some embodiments, the first device 11 and the third device 13 respectively comprise a plug-in connector.

Referring to FIG. 1, the mask 1 comprises a fixing member 10 configured to hold the mask 1 onto a face. In some embodiments, the mask 1 can include ear loops. In some embodiments, the mask 1 includes a retaining strap. In some embodiments, the mask 1 includes resilient bands.

In at least one embodiment, the mask includes an ultrasonic device. A user can wear the mask to clean teeth without using a hand, thereby allowing greater convenience.

It will be apparent to those skilled in the art that various modifications and variations can be made to the disclosed embodiments. It is intended that the specification and examples be considered as exemplary only, with a true scope of the disclosure being indicated by the following claims and their equivalent.

What is claimed is:

1. A foldable and flexible ultrasonic vibration mask for cleaning teeth, comprising:
   a first device comprising a flexible substrate, a plurality of first coils formed on the flexible substrate and configured to generate ultrasonic waves, at least one second coil formed on the flexible substrate and configured to generate audible sound, and a resonance chamber including magnetic alloy materials disposed correspondingly to the first coils and the second coil, wherein the flexible substrate is attached to the resonance chamber;
   a second device comprising a flexible substrate, a plurality of coils configured to generate ultrasonic waves and formed on the flexible substrate of the second device, and a resonance chamber including magnetic alloy materials disposed correspondingly to the coils of the second device, wherein the flexible substrate of the second device is attached to the resonance chamber of the second device, and the flexible substrate of the first device is attached to the flexible substrate of the second device;
   a third device comprising a flexible substrate, a plurality of first coils configured to generate ultrasonic waves and formed on the flexible substrate of the third device, at least one second coil configured to generate audible sound and formed on the flexible substrate of the third device, and a resonance chamber including magnetic alloy materials disposed correspondingly to the first coils and the second coil of the third device, wherein the flexible substrate of the third device is attached to the resonance chamber of the third device, and the flexible substrate of the third device is attached to the flexible substrate of the first device; and a fourth device comprising a flexible substrate, a plurality of coils configured to generate ultrasonic waves and formed on the flexible substrate of the fourth device, and a resonance chamber including magnetic alloy materials disposed correspondingly to the coils of the fourth device, wherein the flexible substrate of the fourth device is attached to the resonance of the fourth device, wherein the flexible substrate of the fourth device is attached to the flexible substrate of the second device, and the flexible substrate of the fourth device is attached to the flexible substrate of the third device.

2. The foldable and flexible ultrasonic vibration mask of claim 1, wherein each of the first, second, third, and fourth devices comprises a chip coupled with the corresponding first coils and the corresponding second coil or coupled with the corresponding coils.

3. The foldable and flexible ultrasonic vibration mask of claim 2, wherein each chip comprises a universal signal and function generator configured to generate at least one of a sine waveform, a square waveform, a saw tooth waveform, or a pulse waveform, and to control a vibration frequency, a vibration time, and a duty cycle of a waveform.

4. The foldable and flexible ultrasonic vibration mask of claim 2, wherein each chip comprises a non-volatile memory.

5. The foldable and flexible ultrasonic vibration mask of claim 4, wherein the non-volatile memory is configured to store a music file.

6. The foldable and flexible ultrasonic vibration mask of claim 5, wherein the chip is configured to convert the music file into an audio signal.

7. The foldable and flexible ultrasonic vibration mask of claim 6, wherein each chip comprises an amplifier configured to amplify the audible signal or an ultrasonic signal.

8. The foldable and flexible ultrasonic vibration mask of claim 1, wherein the first coils, the second coil, or the coils comprise gold, chromium and nickel; or the first coils, the second coil, or the coils comprise silver.

9. The foldable and flexible ultrasonic vibration mask of claim 1, wherein each resonance chamber comprises a magnetic alloy plate.

10. The foldable and flexible ultrasonic vibration mask of claim 9, wherein the magnetic alloy plate comprises iron, cobalt and nickel.

* * * * *